United States Patent [19]

O'Connell et al.

[11] Patent Number: 4,773,968

[45] Date of Patent: Sep. 27, 1988

[54] N-BUTANE/ISOBUTANE FRACTIONATION

[75] Inventors: Harry E. O'Connell, Houston; James O. Nye, Friendswood, both of Tex.

[73] Assignee: Enterprise Products Company, Houston, Tex.

[21] Appl. No.: 940,770

[22] Filed: Dec. 12, 1986

[51] Int. Cl.$^4$ .................. B01D 1/28; B01D 3/14
[52] U.S. Cl. ........................ 203/26; 203/98; 203/DIG. 4; 62/32; 202/202; 585/800
[58] Field of Search .............. 203/26, DIG. 4, 98, 203/88; 202/202; 62/28, 30, 26, 31, 34, 32; 585/800

[56] References Cited

U.S. PATENT DOCUMENTS

| | | | |
|---|---|---|---|
| 2,619,814 | 12/1952 | Kniel | 62/175.5 |
| 3,002,358 | 10/1961 | Dierl | 62/23 |
| 3,225,550 | 12/1965 | Kelley et al. | 62/21 |
| 3,225,551 | 10/1965 | Kelley et al. | 62/21 |
| 3,229,471 | 1/1966 | Palen et al. | 62/21 |
| 3,390,531 | 7/1968 | Bergo et al. | 62/28 |
| 3,509,728 | 5/1970 | Mercer | 62/28 |
| 4,022,597 | 5/1977 | Bacon | 62/28 |
| 4,023,946 | 5/1977 | Schwartzman | 62/26 |
| 4,230,535 | 10/1980 | Howard | 203/26 |
| 4,277,268 | 7/1981 | Spangler, Jr. | 62/26 |
| 4,280,880 | 7/1981 | Vora et al. | 203/23 |
| 4,336,046 | 6/1982 | Schorre et al. | 62/28 |
| 4,357,153 | 11/1982 | Erickson | 62/34 |
| 4,395,310 | 7/1983 | Idenden | 203/26 |
| 4,539,076 | 9/1985 | Swain | 203/26 |
| 4,559,108 | 12/1985 | Ahlberg | 202/154 |

OTHER PUBLICATIONS

P. S. O'Neill, et al., "Vapor Recompression Systems with High Efficiency Components", CEP, Jul., 1985, pp. 57-62.
J. Flores, et al, "Recompression Saves Energy", Hydrocarbon Processing, Jul., 1984, pp. 59-62.
G. P. Quadri, "Use Heat Pump for P-P Splitter", Hydrocarbon Processing, Feb. 1981, pp. 119-126, Mar. 1981, pp. 147-151.

Primary Examiner—Wilbur Bascomb
Attorney, Agent, or Firm—Kenneth H. Johnson

[57] ABSTRACT

An n-butane/isobutane splitter is operated by compressing the isobutane overhead to increase its condensing temperature, using the compressed overhead to heat bottoms in a reboiler, which is operated to condense the overhead and cooling the condensed overhead to a temperature no lower than the temperature on the top tray of the splitter and no higher than 20° F. above the temperature on the top tray, whereby the throughput of the splitter is increased by 10 to 20%.

11 Claims, 1 Drawing Sheet

N-BUTANE/ISOBUTANE FRACTIONATION

BACKGROUND OF THE INVENTION

1. Field of the Invention

The present invention relates to a process for the separation of normal butane and isobutane by fractionation. More particularly the invention relates to the operation of an n-butane/isobutane splitter employing compressed overheads to heat reboiler bottoms to provide a portion of the energy used for the fractionation.

2. Related Art

The use of heat exchange (usually indirect) of one stream to heat another is widely practiced. For example in U.S. Pat. No. 2,619,814 (Kniel) the reboiler may be heated by compressed overheads, in U.S. Pat. No. 3,509,728 (Mercer) compressed overheads heated an evaporator and in U.S. Pat. No. 4,022,597 (Bacon) overheads and bottoms are used to heat incoming feed.

In the last several years n-butane/isobutane splitters, i.e., fractionation units used to separate n-butane from isobutane, have employed heat pumps to increase the pressure of the overhead vapors, thereby increasing the condensing temperature of the vapors, which are then heat exchanged with bottoms from the column in a reboiler to recover some of the heat and use it to drive the distillation, e.g., U.S. Pat. No. 4,559,108 to Ahlberg discloses a $C_4$ fractionation wherein the overhead is split, a portion is compressed, used to heat the bottoms, then recombined with the uncompressed portion, cooled and collected for product recovery and/or reflux.

Similar types of procedures have been described for various hydrocarbon separations, e.g., U.S. Pat. No. 4,230,535 to Howard discloses that two close boiling chemicals may be separated by removing an overhead vapor stream, condensing a portion of the vapor, heating the vapor stream then compressing the heated vapors and supplying heat to a reboiler by condensing a portion of the compressed vapor stream; U.S. Pat. No. 3,002,358 to Dierl discloses a propylene distillation wherein a portion of the overhead is compressed and used to heat two reboilers and a portion returned to the column as reflux; and U.S. Pat. No. 4,277,268 to Spangler, Jr. discloses a fractionator split into a stripping section and a rectifying section wherein the overhead vapors from the rectifying section are heat exchanged with the bottoms of the stripping section.

For economic reasons the system of using the increase in condensation temperature which results from compression to heat the bottoms and provide boil up can only be employed in those systems where the bottoms temperature and the overhead temperature are not widely different such as n-butane/isobutane and propane/propylene separations.

Operation of a conventional n-butane/isobutane splitter may employ a heat pump to compress a portion of the overheads to thereby raise the condensing temperature of the overheads which are then heat exchanged in a reboiler with a portion of the bottoms to provide heat for the boil up in the column. The contact in the reboiler condenses the overheads which are accumulated, with a portion being yielded to isobutane product and a portion being returned as reflux to the splitter (fractionating column) Reflux is returned to the column as a mixture of vapor and liquid, usually on to or above the first tray. Even though the temperature gradient along the splitter is generally less than 35° F., the pressure of the overheads needs to be 50–100 psi or more, to provide a sufficient temperature differential in the reboiler (heat exchanger) to maintain the temperature in the bottom of the column for boil up and to drive the fractionation.

In the prior operation the temperature of the reflux is such that around 17% of the reflux was vaporized on the top tray, which increased the vapor from the top tray by that amount and increased the flow through the compressor, correspondingly.

In the present invention it was found that reducing the temperature of the reflux to a temperature no lower than the temperature on the top tray and no higher than about 20° F. greater than the temperature on the top tray, reduces the amount of reflux vaporized and allows the column to be operated at higher throughputs, hence increasing the columns' efficiency. Reflux returned to the tower is less likely to vaporize if the temperature is closer to the temperature on the top tray but no lower than temperature on the top tray.

SUMMARY OF THE INVENTION

Briefly, the present invention is a fractional distillation for the separation of isobutane from normal butane in which the overhead is compressed to increase its condensing temperature with the compressed overhead then being used to heat the bottoms to provide the boil up while the overheads are condensed. The compressed overheads are condensed in the reboiler by heat exchange with a portion of the bottoms, then a portion of the condensed overheads are subsequently cooled and returned to the fractional distillation as reflux. The temperature of the reflux must be at least as high as the top of the tower, i.e., the temperature on the first tray, in order to avoid overcondensing vapor coming to the top tray, e.g., flooding, but no higher than about 20° F. greater than the temperature at the top of the tower, preferably no higher than 15° F. greater than the temperature at the top of the tower. The higher the temperature of the reflux (above the temperature of the top tray) the more it is volatilized with an undesirable increase in the vapors in the overhead, which in effect reduces the throughput capacity of any given unit. Economic considerations play a part in adapting any system to the present invention. Hence the amount of cooling which can be justified economically (i.e., energy expense) must be balanced with the benefit of increased throughput (i.e., energy saving). Thus, although a temperature as close to and slightly above that at the top of the column is most desirable, realistically a temperature within 20° F. of that temperature provides substantial benefits since uncooled reflux will be well in excess of this, e.g. 30° F. or greater than the temperature of the top tray. Generally an n-butane/isobutane splitter is operated at 50 to 100 psig with corresponding overhead temperature of 90° to 103° F. and bottoms temperature of 123° to 140° F.

After the overhead is condensed it is accumulated and a portion then is directed back to the column as reflux (the remainder is isobutane product). The condensed overhead is usually well above the temperature at the top of the tower at this point, e.g., 30° F. or greater. Feeding this material back as reflux can result in 10 to 20% less capacity for a given n-butane/isobutane splitter.

More specifically, the present invention is a process for separating isobutane from n-butane by fractionation comprising feeding a hydrocarbon stream consisting essentially of isobutane and n-butane to a fractionation zone (i.e., column) preferably having therein a plurality of trays. Heat is supplied to said fractionation zone to vaporize said isobutane and to provide an overhead stream consisting essentially of isobutane, vapor. The overhead vapor stream is compressed to increase the condensing temperature thereof to a temperature sufficiently greater than the temperature of the bottoms of said fractionation zone (generally 10° to 20° F. increase in the condensing temperature) whereby indirect contact of said compressed overheads with a portion of the bottoms from said fractionation zone increases the temperature of the bottoms portion to (1) vaporize said portion of the bottoms, (2) provide boil up in said fractionation zone, and (3) condense said compressed overhead. The condensed overhead are recovered and a portion of the condensed overhead are cooled to a temperature no less than the temperature at the top of the column, preferably no less than the temperature on the top tray if trays are present and no greater than 20° F. above the temperature at the top of the column. The portion of cooled condensed overhead is returned to the top of the column as reflux.

The indirect contact in the reboiler is preferably achieved by maintaining a liquid level of condensed overheads in a reboiler/condenser, said liquid level being adjusted to extract a maximum amount of heat from the compressed overheads to give the lowest temperature leaving the reboiler When the term "tray" is used herein, it includes all of the various types of internal structures used for intimately contacting gases and liquid, such as tray columns, including cross-flow plate and counterflow plate types, bubble cap columns, inert packing materials and the like. In these conventional systems, the reflux is returned to the top of the column and usually on to the top tray, plate, cap or the like.

PREFERRED EMBODIMENT AND DETAILED DESCRIPTION OF THE INVENTION

Figure 1:
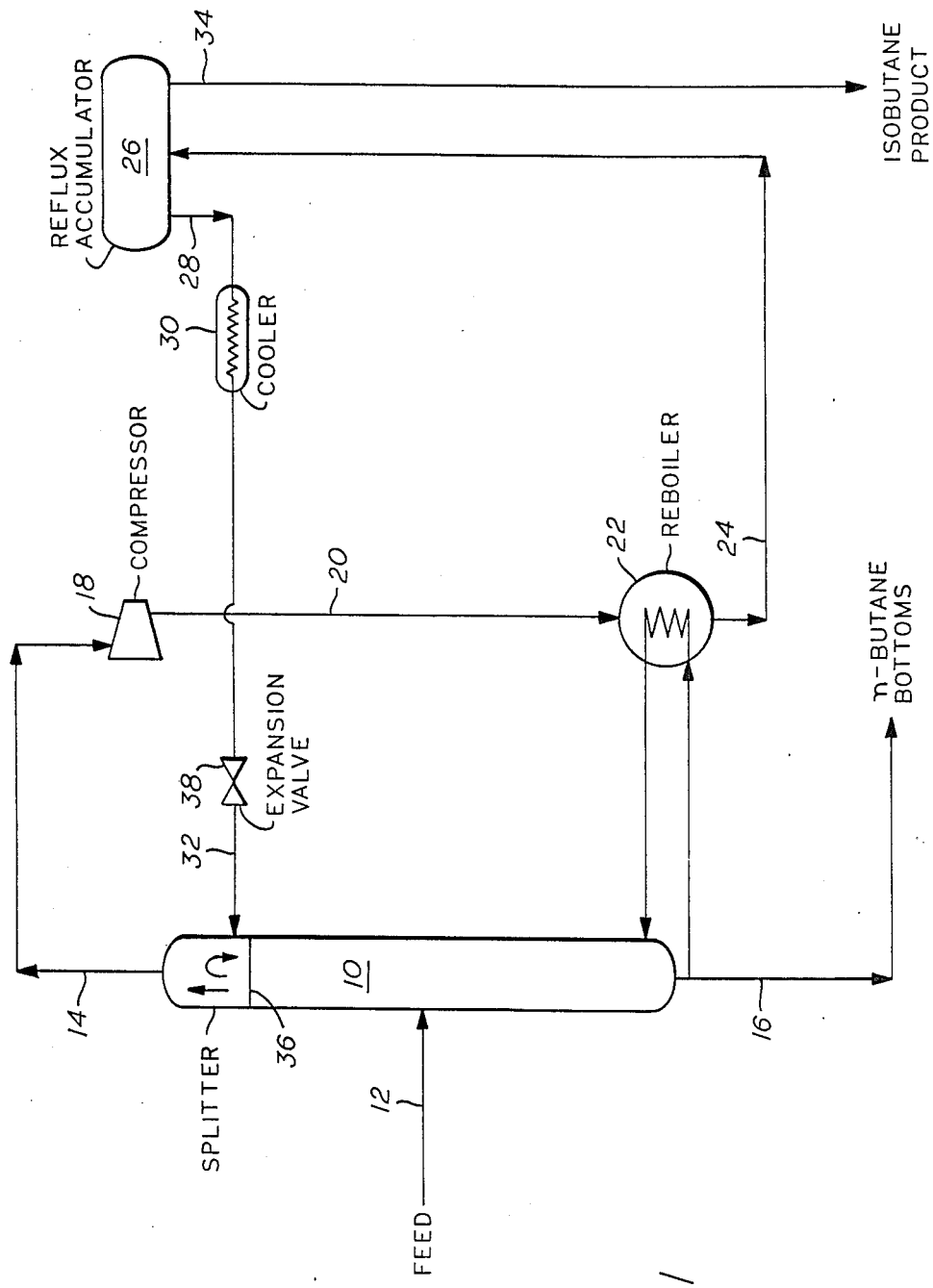
FIG. 1 is a diagrammable flow sheet of the process of the present invention.

FIG. 1 provides a flow diagram of the present process. The feed, predominantly a $C_4$ stream of n-butane and isobutane enters the fractionation column 10 via line 12. The column preferably has conventional sieve trays, preferably about 80 trays. The feed enters the column in the upper middle quadrant, although it could be fed at different points, just as other types and numbers of trays can be used.

The heat for the fractionation is supplied by compressing the overhead vapors in compressor 18 then using the compressed overhead vapors to heat the bottoms circulating from column 10 through the reboiler 22. When heated to the appropriate temperature for the pressure conditions in the column, the lower boiling isobutane (and lighter hydrocarbons) will vaporize and ascend upward through the column while the heavier materials, n-butane (any $C_5$ or heavier hydrocarbons) will descend through the column to form the bottoms which are removed via line 16. The vapor rising will tend to concentrate the isobutane, such that by the time it reaches the top of the column it has concentrated to the point where it is high purity isobutane and a high purity n-butane bottoms.

Since both n-butane and isobutane are gases at atmospheric pressure, the use of a pressured system is essential to being able to carry out a fractional distillation. The column may be operated at pressures between 50 and 100 psig, preferably 60 to 80 psig. The heat pump system using compressed overheads to supply heat for the reboiler only works where the temperature differential between the overhead and the bottoms is close, as it is in the case of n-butane and isobutane. The temperature differential (overheads to bottoms) in a commercial n-butane/isobutane splitter is about 23° to 35° F.

Thus by heating the mixed n-butane and isobutane under pressure in the column as described the overhead 14 is recovered as high purity isobutane. The overhead is compressed in compressor 18 whereby energy in the form of heat is added to the vaporous overhead by mechanical work (compression). The compressed isobutane overhead 20 is now at a pressure sufficiently high to give a condensing temperature to heat the reboiler 22, that is, to provide the heat source to heat the liquid in the reboiler sufficiently to provide all of the heat (boil up) needed to sustain the fractionation. Even though energy is required to operate the compressor it is less than that required to operate a conventional distillation without compression.

When the compressed overheads indirectly contact the bottoms fraction the overheads are condensed and the condensed overheads sent via 24 to accumulator 26 where a portion is yielded as isobutane product 34 and a portion 28 sent to cooler 30.

According to a preferred embodiment the liquid level and the rate of condensed overheads flow in the reboiler 22 are adjusted to permit the lowest temperature of the condensed overheads leaving the reboiler, while maintaining the condensing capacity of the reboiler at its maximum. Precise control of the condensate level can maximize the degree of condensation being obtained while also obtaining the lowest temperature of the condensate leaving the reboiler.

From the compressor 18 through cooler 30 the pressure in the system is substantially greater than the pressure in the fractionation column. Hence, an expansion valve 38 (or other device for this purpose) is provided to allow for the cooled reflux stream 32 to adjust to the pressure of the column. In prior operation where the reflux had not been cooled as taught herein, the reduction of the pressure at the expansion valve resulted in a substantial vaporization of the reflux even before it was returned to the tower. This vapor combined with the flash vaporization of the overheated liquid portion of the reflux results in a substantial incidental overhead vapor burden, which when reduced according to the present invention increases the capacity of the same equipment.

The reflux 32 is returned to the top of column which in this embodiment is on the top tray 36. An isobutane product 34 is yielded from accumulator 26.

Such conventional items as pumps, valves, drains and the like are omitted from the flow diagram but their location and functioning is obvious to those in the art. In a conventional n-butane/isobutane splitter the volume of overheads is in excess of that required for heating the bottoms thus a trim condenser was employed to condense this excess, however, the system according to the present invention does not require a trim condenser.

Current fractionating skill allows very narrow and precise cuts to be taken. Hence the feed to the n-butane/isobutane splitter is predominantly $C_4$ with less than 5 vol. % total heavier and/or lighter hydrocarbons. The present invention is designated for the separation of a C$_4$ stream containing isobutane and normal butane as its principal components. Generally, a feed suitable for this procedure would contain 5 to 95 mole % isobutane, 5 to 95 mole % n-butane, 0 to 20 mole % butenes, 0 to 5 mole % C$_3$'s and lighter, and 0 to 5 mole % C$_5$'s and heavier. Preferably, the feed will contain 20 to 80 mole % isobutane and 20 to 80 mole % n-butane with less than 1 to 3 mole % C$_3$'s and 1 to 3 mole % C$_5$'s and heavier. One source of suitable feed to the splitter 10 is the overheads from a debutanizer.

In order to demonstrate the improvement obtained according to the present invention a comparison between the splitter operated with reflux cooled in accordance with the invention and in the prior manner is presented. In the TABLE the two operations are compared at various points along the flows. The feed used in these examples contained 36.8 mole % isobutane, 61.6 mole % n-butane, 1.2 mole % propane and 0.4 mole % isopentane. For this illustration the overhead flow is constant for both operations (compressor capacity) and the temperature in the accumulator is the same. The distinction in the two operations can be seen in the Table wherein the vaporized reflux, according to the present invention is only 99,000 lbs./hr vapor compared to 204,000 lbs./hr vapor reflux in the prior operation. This coupled with the reduction in the flashing of the cooler liquid portion of the reflux, allows an additional 29,546 pounds per hour of feed to the column at the same overhead flow rates, which is about an 10% increase in feed over the prior operation. The internal reflux for both illustrations is also the same. Internal reflux = Liquid reflux in the column/isobutane product.

The separation was substantially the same in both cases with isobutane purity in excess of 95 mole %.

temperature sufficiently greater than the temperature of the bottoms of said fractionation zone to provide said heat for said fractionation;

(d) indirectly contacting all of said compressed overheads with a portion of the bottoms from said fractionation zone to increase the temperature of said bottoms portion to:
 (i) vaporize said portion of the bottoms,
 (ii) provide boil up in said fractionation zone, and
 (iii) condense all of said compressed overheads;

(e) cooling a portion of the condensed overheads to a temperature no less than the temperature at the top of said fractionation zone and no greater than 20° F. above the temperature at the top of said fractionation zone; and (f) returning said cooled portion of condensed overhead to the top of said fractionation zone as reflux.

2. The process according to claim 1 wherein the pressure in the fractionation zone is in the range of 50 to 100 psig.

3. The process according to claim 2 wherein the temperature at the top of the fractionation zone is in the range of 90° to 103° F.

4. The process according to claim 3 wherein the temperature in the bottom of the fractionation zone is in the range of 123° to 140° F.

5. The process according to claim 1 wherein said fractionation zone comprises a fractionation column having a plurality of trays and said top of said fractionation zone comprises the top of said plurality of trays.

6. The process according to claim 5 wherein the temperature of said cooled portion of condensed overhead is no less than the temperature on the top tray and no greater than 20° F. above the temperature on the top tray.

7. The process according to claim 1 wherein said

TABLE

| | STREAM NO. | | | | | | |
|---|---|---|---|---|---|---|---|
| | 12 | 14 | 20 | 28 | 32 | 34 | |
| | | | | Descr. | | | |
| | Feed | Overhead | Compressed Overhead | Condensed Overhead | Reflux | Tower Bottoms | Isobutane Product | Internal Reflux |
| | | | Prior Operation | | | | | |
| Lbs/Hr | 306,041 (36,500 bbl/day) | 1,300,000 | 1,300,000 | 1,300,000 | 1,185,000 (981,000 Liq) (204,000 Vap) | — | 115,004 | 8.5 |
| Pressure, Psig | — | 66 | 139 | 137 | 66 | — | | |
| Temp, °F. | — | 92 | 150 | 130 | 130 | 125 | | |
| | | | Invention | | | | | |
| Lbs/Hr | 335,587 (40,000 bbl/day) | 1,300,000 | 1,300,000 | 1,300,000 | 1,174,000 (1,075,000 Liq) (99,000 Vap) | — | 126,107 | 8.5 |
| Pressure, Psig | — | 66 | 129 | 127 | 66 | — | | |
| Temp, °F. | — | 92 | 144 | 137 | 110.7 | 125 | | |

The invention claimed is:

1. A process for separating isobutane from a mixture of isobutane and n-butane by fractionation comprising:
 (a) feeding a hydrocarbon stream consisting essentially of isobutane and n-butane to a fractionation zone;
 (b) supplying heat to said fractionation zone to vaporize said isobutane and to provide an overhead stream consisting essentially of isobutane vapor;
 (c) compressing all of said overhead vapor stream to increase the condensing temperature thereof to a condensed overheads are maintained at a liquid level during said indirect contacting to extract a maximum amount of heat therefrom by said bottoms portion.

8. The process according to claim 1 wherein said cooled, condensed and compressed overheads are passed through an expansion zone to reduce the pressure thereof to that of the fractionation zone.

9. The process according to claim 1 wherein the overheads are compressed to increase the condensing temperature thereof to a temperarure of 10° to 20° F.

above the temperature of the bottoms portion of the fractionation zone.

10. The process according to claim 1 wherein the temperature of the reflux is no greater 15° F. above the temperature at the top of said fractionation zone.

11. A process for separating isobutane from a mixture comprising isobutane and n-butane by fractionation comprising:
   (a) feeding a hydrocarbon stream consisting essentially of isobutane and n-butane to a fractionation zone maintained at a pressure in the range of 50 to 100 psig, a temperature at the top of the fractionation zone in the range of 90° to 103° F. and at the bottom of the fractionation zone in the range of 123° to 140° F.;
   (b) supplying heat to said fractionation zone comprising a plurality of trays to vaporize said isobutane and to provide an overhead stream consisting essentially of isobutane vapor;
   (c) compressing all of said overhead vapor stream to increase the condensing temperature thereof to a temperature in the range of 10° to 20° F. greater than the temperature of the bottoms of said fractionation zone;
   (d) indirectly contacting all of said compressed overheads with a portion of the bottoms from said fractionation zone to increase of the temperature of said bottoms portion to:
      (i) vaporize said portion of the bottoms,
      (ii) provide boil up in said fractionation zone, and
      (iii) condense all of said compressed overhead;
   (e) cooling a portion of the condensed overhead to a temperature no less than the temperature at the top tray of said fractionation zone and no greater than 20° F. above the temperature at the top tray of said fractionation zone;
   (f) passing said cooled condensed overhead through an expansion zone, and
   (g) returning said cooled portion of condensed overhead to the top of said fractionation zone as reflux.

* * * * *